United States Patent [19]

Teng et al.

[11] 4,193,989

[45] Mar. 18, 1980

[54] SUNSCREEN GEL

[75] Inventors: James Teng, St. Louis County; James M. Lucas, Crestwood; Marcella C. Stubits, St. Louis, all of Mo.

[73] Assignee: Anheuser-Busch, Incorporated, St. Louis, Mo.

[21] Appl. No.: 727,169

[22] Filed: Sep. 27, 1976

[51] Int. Cl.$^2$ .......................... A61K 7/42; A61K 7/44
[52] U.S. Cl. ......................................... 424/60; 424/47; 424/59; 424/64; 424/362
[58] Field of Search ............... 424/59, 60, 363, 362

[56] References Cited

U.S. PATENT DOCUMENTS

| | | | |
|---|---|---|---|
| 3,485,915 | 12/1969 | Gerstein | 424/65 X |
| 3,824,085 | 7/1974 | Teng | 44/7 B |
| 3,940,384 | 2/1976 | Teng | 536/66 |

FOREIGN PATENT DOCUMENTS

| | | | |
|---|---|---|---|
| 571216 | 2/1959 | Canada | 424/60 |
| 1029342 | 3/1953 | France | 424/60 |
| 2034415 | 12/1970 | France . | |

OTHER PUBLICATIONS

Teng et al., Cosmetics & Perfumery, 10/1975, vol. 90, pp. 32, 34, 36, 40, 42 and 43.
American Perfumes & Cosmetics, 1975, vol. 86, pp. 8.

*Primary Examiner*—Dale R. Ore
*Attorney, Agent, or Firm*—Graveley, Lieder & Woodruff

[57] ABSTRACT

A water-resistant suntan gel comprising an alcoholic solvent, a sunscreen agent, emollients, a selected acid which enhances the binding ability of the gel film to the skin and a gelling agent for the solvent. The composition prevents sun damage to the skin and promotes an even tan. The composition forms a film on the skin, which film is water insoluble yet easily removable.

5 Claims, No Drawings

SUNSCREEN GEL

BACKGROUND OF THE INVENTION

Radiation in the range 2900 to 3150 Å exerts the most profound effects on the human body. The production of vitamin D in the skin by irradiation of the provitamin 7-dehydrocholesterol, the generation of a more or less intense and often painful erythema followed by reversible pigmentation, the wrinkling, creasing, and aging of the skin all result from different degrees of exposure of the human body to sunlight. Aside from these "normal" responses, there are also a considerable number of skin and systemic malfunctions which can be adversely affected by irradiation with ultraviolet and visible range electromagnetic radiation. (Kreps and Goldemberg, *Cosmetics: Science and Technology* Vol. 1, Balsam, et al Ed., John Wiley & Sons, Inc., 1972 p. 247).

Clinicians concerned with these damaging effects recommend the more widespread use of ultraviolet screening preparations as a preventive measure on a continuing basis, at least for fair-complexioned individuals, not only to prevent cancer but to prevent premature aging and wrinkling of the skin as well. (Kreps and Goldemberg, p. 256).

The only practical technique for preventing sunburn is to limit the exposure of the skin to the erythemogenic range of electromagnetic radiation to dosages less than those required to produce the harmful effect. This may be accomplished by avoiding exposure of the individual for more than the shortest period of time. Such limitations do not, however, fit into the designs of persons who enjoy outdoor activity and admire darkening of the skin acquired through exposure to sunlight. Avoidance of exposure is not necessary because the effects of the exposure may be reduced readily by the use of cosmetic agents which, applied to the skin, attenuate the dosage of erythemogenic radiation reaching the skin. This desired attenuation may be achieved either by reflection of the radiation by a coating on the skin or by absorption of the erythemogenic energy by the coating before it can fall on the surfaces of the skin. (Kreps and Goldemberg, p. 262)

The present invention is concerned with absorption of the erythemogenic energy by a coating before it reaches the skin. Aside from the proper electronic structure to establish the wavelength of maximum absorptivity in the erythemal range, the successful screening material must also have a distinct cutoff so that it transmits wavelengths above the erythemal range, it must show resistance to chemical and photochemical changes in structure, it should undergo minimum absorption through the skin, it should be sufficiently soluble in conventional cosmetic vehicles but it should be relatively insoluble in water or perspiration, it should be essentially free of toxic, irritating or sensitizing properties, and it should be essentially self-plasticizing in use. (Kreps and Goldemberg, p. 268).

Customary vehicles for sunscreens are hydroalcoholic lotions, water-in-oil or oil-in-water emulsions, and oily lotions. It is essential that the sun-screening compound shall be dissolved or dispersed easily and permanently in the vehicle. Once it is spread on the skin, it should remain in place as a continuous film, closely adhering to the surface, and it should resist washing off either by perspiration or by immersion in fresh or salt water.

Screens with limited solubility in the vehicle may crystallize during shelf storage in the container, or they may be thrown out of solution during shipment through cold-weather areas. Some materials may be unusuable because they cannot be dissolved in effective concentrations. The concentrations are often higher than the nominal concentration of the total suntan preparation; the concentration of the screen in the nonvolatile residual film left on the skin after evaporation of the volatile ingredients may be as high as 30 to 40% and higher in the case of simple hydroalcoholic lotions. If the screen crystallizes or separates from the other ingredients at these concentrations, the coverage of the skin may be patchy and the resulting protection afforded by the preparation may be incomplete.

The solubility of a screen in water or in perspiration generally implies that the film can be washed off the skin easily, with a consequent loss of protection. The film deposited on the skin is so small, however, that even slightly water-soluble screens are readily removed. After a few minutes of swimming on a fresh water pool, 90 to 99% of the screen is removed from the skin, and the amount of screen that remains is not effective. This is essentially independent of the nature of the carrier vehicle, although it appears that the swim removes an oily film more completely than it does a film deposited from a hydroalcoholic lotion. (Kreps and Goldemberg, p. 270).

Varied cosmetic bases have been employed to carry the sunscreen, and the makeup of the vehicle affects the efficacy of the product. Creams, cream lotions, oils, gels, hydroalcoholic lotions, jellies, lipsticks, and aerosol foams and sprays are common formulations which comprise the primarily cosmetic suntan preparations. Dermatologists often prefer ointments as the vehicle of choice, and they have also recommended the inclusion of sunscreens in makeup and hair preparations to prevent solar damage. (Kreps and Goldemberg, p. 285).

The formulations set forth below reveal gels and jellies that are prominent in the prior art.

JELLY

The anhydrous jelly shown below contains no emulsifier and hence is exceptionally difficult to wash off. Erythemal transmission of this preparation is only 2.1 percent, but the tanning range is transmitted to the extent of 54.5% of the incident energy. The red veterinary petrolatum and the sesame oil in the cosmetic base, used in the quantities shown, contribute to the ultraviolet absorption of this preparation.

| JELLY COMPOSITION | |
|---|---|
| Red veterinary petrolatum | 40.2% |
| Sesame oil | 36.0 |
| Ozokerite | 2.8 |
| Mineral oil 38/40 | 20.0 |
| Escalol 506 | 1.0 |

GEL

Dihydroxyacetone is a skin stainer which reacts with most primary amines, including the amino acids of the skin. It does not have any significant ultraviolet absorption in the erythemal range, nor does the dye which it forms with amines. The color takes about 3 to 5 hours to develop. The formula below indicates one method of its use in a quick-tanning clear gel. Carbopol 940 operates as the emulsifying agent in the gel formulation. The Uvinul D-50 functions merely to protect the Carbopol from light degradation and does not contribute to the functional erythemal absorption. (Kreps and Goldemberg, p. 299).

| GEL COMPOSITION | |
|---|---|
| Part A | |
| Ethanol | 25.00% |
| Escalol 506 | 1.20 |
| Ceraphyl 230 | 2.00 |
| Uvinul D-50 | 0.07 |
| Part B | |
| Water | 26.23 |
| Dihydroxyacetone | 3.00 |
| Part C | |
| Carbopol 940 | 1.50 |
| Part D | |
| Foamole L | 4.00 |
| Ethanol | 17.00 |
| Water | 20.00 |

It is an object of this invention to produce a sun-tan formulation with controlled viscosity for the purpose of ease of application to the skin.

It is a further object of this invention to produce a sun-tan formulation which is characterized by a water insoluble film so as to create a longer lasting effect.

It is still a further object to produce a sun-tan formulation that is characterized by an alcoholic solution so that multiple coatings can readily be applied.

The composition of the present invention prevents sun-damage to skin, and promotes an even tan (due to the adherence of the film on the skin). The film is water insoluble, so that the product has the same protective action during and after swimming. Yet, it is easily removed by washing with soap and water. The non-greasy product does not stain cloth or towels. The product contains emollients and skin softening protein for easy smooth-on. Because of the continuous film spread on the skin the product is efficient in retarding moisture loss.

SUMMARY

This invention involves water-resistant suntan lotion containing a gelling agent. The composition comprises an alcoholic solvent, a sunscreen agent, emollients, a selected acid which enhances the binding ability of the gel film to the skin and a gelling agent for the solvent. The gelling agent is hydroxypropyl cellulose acetate.

DETAILED DESCRIPTION

The sunscreen preparation of the present invention comprises a solvent, an ultraviolet radiation absorber, an emollient, and a gelling agent. The preparation may also contain a protein, a chelating agent, and a plasticizer.

Ethanol SD 40 functions as the solvent for the ingredients of the composition. A suitable substitute for ethanol is isopropyl alcohol. About 80% (w/w) to about 90% (w/w) solvent is used.

Citric acid is employed to enhance the binding ability of the film to the skin. Adipic acid, succinic acid, and malic acid may be used in lieu of citric acid. About 1% (w/w) to about 3% (w/w) binding agent is used.

Propylene glycol dipelargonate is an emollient and acts as a lubricant to prevent the film from rubbing off the skin. Other suitable emollients are myristyl lactate, lauryl lactate, and decyl oleate. About 3% (w/w) to about 7% (w/w) emollients are used.

Teng et al, U.S. Pat. No. 3,824,085 discloses the gelling agents to be used in this invention. Basically, the gelling agent is a polymeric carbohydrate derivative selected from the group consisting of hydroxypropyl cellulose esters and hydroxypropyl starch esters and mixtures of these esters. These esters can have a D.S. of about 1.2 to about 3 and a M.S. of hydroxypropyl groups of about 2 to about .8. Suitable esters are:
hydroxypropyl cellulose acetate
hydroxypropyl starch acetate Teng et al, U.S. Pat. No. 3,940,384 discloses another gelling agent which can be used in this invention. This gelling agent is methyl hydroxypropyl cellulose acetate. This ester has a D.S. of acetyl groups of about 0.8 to about 2.5 and a M.S. of hydroxypropyl groups of about 2 to about 8. The D.S. of methyl groups is about 0.1 to about 1.0.

The important physical properties of the gelling agent are summarized in Table 1. The usual form is that of a white powder of 20–40 mesh. Depending upon the equipment, the particle size can be varied. The material is basically not hydroscopic and therefore has low moisture content.

The gelling agents are highly substituted derivatives and are generally inert to enzymatic activity.

TABLE 1

| Physical Properties of Gelling Agent | |
|---|---|
| Color | White |
| Physical Form | Soft powder, 20–40 mesh |
| Moisture | 0.5% |
| Ash | 1.0% |
| Specific Gravity | 1.017 |
| Glass Transition Temperature | 85° C. |
| Melting Range | 190°–210° C. |
| Char Point | 240° C. |
| Biological Activity | Does not support microbial growth. Inert to proteolytic amylolytic degradation. |

About 1% (w/w) to about 2% (w/w) gelling agent is used.

Amyl-p-dimethylaminobenzoate is generally used as the active ingredient to absorb ultraviolet radiation. Suitable substitutes for this compound are glycerol mono-p-amino benzoate, homomenthyl salicylate, and 2 ethoxy ethyl-p-methoxycinnamate. About 1% (w/w) to about 12% (w/w) ultraviolet absorbing agent is used.

The film can be removed by simple washing with soap and water.

The film is water-resistant. It will not become tacky upon drying and does not rub off from the skin when wetted with water.

EXAMPLE I

The following ingredients are mixed together in the listed amounts:

| Ingredient | Percent By Weight |
|---|---|
| Ethanol, SD 40 | 90 |
| Citric acid | 2 |
| Amyl p-dimethyl aminobenzoate | 2 |
| Propylene glycol dipelargonate | 5 |

-continued

| Ingredient | Percent By Weight |
|---|---|
| Hydroxypropyl cellulose acetate | 1 |

EXAMPLE II

The following ingredients are mixed together in the listed amounts:

| Ingredient | Percent By Weight |
|---|---|
| Ethanol | 87.2 |
| Citric acid | 2.0 |
| Myristyl lactate | 5.8 |
| Amyl p-dimethyl aminobenzoate | 2.0 |
| Silicone Oil | 2.0 |
| Hydroxypropyl cellulose acetate | 1.0 |

The myristyl lactate is an emollient. It imparts a "smoother" feel to the film on the skin. Silicone oil provides more flexibility and water-resistance to the film on the skin.

Amyl-p-dimethylaminobenzoate is the active ingredient which absorbs ultraviolet radiation. This radiation is the cause of sunburn.

Certain esters of salicylate can be used as the ultraviolet radiation absorber.

What is claimed is:

1. A water resistant suntan gel capable of forming, by solvent evaporation, a water-resistant film on skin after application of the gel thereon, which consists essentially of about 80 to about 90% alcoholic solvent, about 1 to about 12% ultraviolet radiation absorber which is soluble in said solvent, about 3 to about 7% emollient, about 1 to about 2% gelling agent for said solvent, said gelling agent being selected from the group consisting of hydroxypropyl cellulose acetate, hydroxypropyl starch acetate, and mixtures thereof, said esters having a degree of substitution of about 1.2 to about 3 and a degree of molar substitution of hydroxypropyl groups of about 2 to about 8, and methyl hydroxypropyl cellulose acetate having a degree of molar substitution of hydroxypropyl groups of about 2 to about 8, a degree of substitution of methyl groups of about 0.1 to about 1, and a degree of substitution of acetyl groups of about 0.8 to about 2.5, and about 1 to about 3% of an acid selected from the group consisting of citric acid, adipic acid, succinic acid and malic acid to enhance the binding ability of said gel film to the skin.

2. The product of claim 1 wherein the gelling agent is hydroxypropyl cellulose acetate.

3. The product of claim 1 wherein the gelling agent is hydroxypropyl starch acetate.

4. The product of claim 1 wherein the ultraviolet radiation absorber is amyl p-dimethyl aminobenzoate.

5. The product of claim 1 wherein the emollient is selected from the group consisting of propylene glycol dipelargonate, myristyl lactate, lauryl lactate, and decyl oleate.

* * * * *